United States Patent
Martin et al.

(10) Patent No.: US 9,250,242 B2
(45) Date of Patent: Feb. 2, 2016

(54) IN VITRO CAPTURE AND ANALYSIS OF CIRCULATING TUMOR CELLS

(71) Applicants: Roche Molecular Systems, Inc., Pleasanton, CA (US); The University of North Carolina at Chapel Hill, Chapel Hill, NC (US)

(72) Inventors: George Martin, Berkeley, CA (US); Steven Soper, Baton Rouge, LA (US); Makgorzata Witek, Chapel Hill, NC (US); Jen Jen Yeh, Chapel Hill, NC (US)

(73) Assignees: ROCHE MOLECULAR SYSTEMS, INC., Pleasanton, CA (US); THE UNIVERSITY OF NORTH CAROLINA, Chapel Hill, NC (US)

( * ) Notice: Subject to any disclaimer, the term of this patent is extended or adjusted under 35 U.S.C. 154(b) by 0 days.

(21) Appl. No.: 14/075,143

(22) Filed: Nov. 8, 2013

(65) Prior Publication Data

US 2014/0134646 A1 May 15, 2014

Related U.S. Application Data

(60) Provisional application No. 61/724,753, filed on Nov. 9, 2012.

(51) Int. Cl.
*G01N 33/574* (2006.01)
*G01N 33/569* (2006.01)
*B01L 3/00* (2006.01)

(52) U.S. Cl.
CPC .... *G01N 33/56966* (2013.01); *G01N 33/57492* (2013.01); *B01L 3/5027* (2013.01); *G01N 2333/96433* (2013.01)

(58) Field of Classification Search
None
See application file for complete search history.

(56) References Cited

U.S. PATENT DOCUMENTS

| | | | |
|---|---|---|---|
| 2010/0210989 A1* | 8/2010 | Macpherson et al. | 604/6.03 |
| 2010/0240081 A1 | 9/2010 | Rollinger et al. | |
| 2010/0255479 A1 | 10/2010 | Mikolajezyk et al. | |
| 2010/0297634 A1 | 11/2010 | Chen | |

FOREIGN PATENT DOCUMENTS

| | | | | |
|---|---|---|---|---|
| WO | 0220825 | A1 | 3/2002 | |
| WO | 2005043121 | A2 | 5/2005 | |
| WO | WO 2008/131048 | * | 10/2008 | G01N 33/569 |
| WO | 2009140326 | A2 | 11/2009 | |
| WO | 2010124227 | A2 | 10/2010 | |
| WO | 2012106658 | A1 | 8/2012 | |
| WO | PCTEP2013073381 | | 1/2014 | |

OTHER PUBLICATIONS

Ostermann et al. (Clin. Cancer Res., 14: 4584-4592, 2008).*
Went et al. (Human Pathology, 35: 122-128, 2004).*
Gilmore et al. (Biochemical and Biophysical Research Communications, 346: 436-446, 2006).*
Edosada, Conrad Yap, et al., 2006, "Selective Inhibition of Fibroblast Activation Protein Protease Based on Dipeptide Substrate Specificity", The Journal of Biological Chemistry, 281(11):7437-7444.
Kennedy, Alanna, et al. 2009, "Elevation of seprase expression and promotion of an invasive phenotype by collagenous matrices in ovarian tumor cells", Int. J. Cancer, 124(1):27-35.
Monskey, Wayne L., et al., 1994, "A Potential Marker Protease of Invasiveness, Separase, Is Localized on Invadopodia of Human Malignant Melanoma Cells", Cancer Research, 54:5702-5710.
Shi, Min, et al., 2012, "Expression of fibroblast activation protein in human pancreatic adenocarcinoma and its clinicopathological significance", World Journal of Gastroenterology, 18(8):840-846.
Brabletz, Thomas, et al., 2005, "Invasion and Metastasis in Colorectal Cancer: Epithelial-Mesenchymal Transition, Mesenchymal-Epithelial Transition, Stem Cells and B-Catenin", Cells Tissues Organs, 179:56-65.
Cristofanilli, Massimo, et al., 2004, "Circulating Tumor Cells, Disease Progression, and Survival in Metastatic Breast Cancer", The New England Journal of Medicine, 351(8):781-791.
Hayes, Daniel F., et a.l, 2008, "Is There a Role for Circulating Tumor Cells in the Management of Breast Cancer." Clinical Cancer Research, 14:3646-3650.
Lu, Janice, et al., 2010, "Isolation of circulating epithelial and tumor progenitor cells with an invasive phenotype from breast cancer patients", International Journal Cancer, 126(3):669-683.
Mego, Michal, et al., 2010, "Molecular mechanisms of metastasis in breast cancer-clinical applications", Clinical Oncology, 7:693.
Pecot, Chad V., et al., 2011, "A novel platform for detection of CK+ and CK-CTCs", Cancer Discovery, 1 (7):580-586.
Raimondi, Cristina, et al., 2011, "Epithelial-mesenchymal transition and sternness features in circulating tumor cells from breast cancer patients", Breast Cancer Research Treatment, 130:449-455.
Sabile, Abdelmajid, et al., 1999, "Efficiency of Ber-EP4 Antibody for Isolating Circulating Epithelial Tumor Cells Before RT-PCR Detection", Journal of Clinical Pathology, 112:171-178.
Sabile, A, et al., 1999, "Efficiency of Ber-EP4 Antibody for Isolating Circulating Epithelial Tumor Cells Before RT-PCR Detection", Journal of Clinical Pathology, 112:171-178.
Sieuwerts, Anieta M., et al., 2009, "Anti-Epithelial Cell Adhesion Molecule Antibodies and the Detection of Circulating Normal-Like Breast Tumor Cells", Journal of the National Cancer Institute, 101:61-66.
Sun, Yun-Fan, et al., 2011, "Circulating tumor cells: advances in detection methods, biological issues, and clinical relevance", Journal of Cancer Research and Clinical Oncology, 137:1151-1173.
Thurm, Holger, et al., 2003 "Rare Expression of Epithelial Cell Adhesion Molecule on Residual Micrometastatic Breast Cancer Cells after Adjuvant Chemotherapy", Clinical Cancer Research, 9:2598-2604.

* cited by examiner

Primary Examiner — Brad Duffy
Assistant Examiner — Nelson B Moseley, II
(74) Attorney, Agent, or Firm — Carol Johns; Olga Kay (57) ABSTRACT

This invention provides methods and compositions for capturing circulating tumor cells (CTCs) as well as various divergent CTC phenotypes using seprase-specific affinity reagents. Methods of analyzing CTCs and assessing their metastatic potential in vivo and in vitro are also disclosed.

23 Claims, 2 Drawing Sheets

IN VITRO CAPTURE AND ANALYSIS OF CIRCULATING TUMOR CELLS

FIELD OF THE INVENTION

This invention relates to the field of cancer biology and more specifically, to methods and compositions for in vitro capture and analysis of circulating tumor cells, the source of cancer metastasis.

BACKGROUND OF THE INVENTION

Metastasis to distal organs causes the majority of cancer deaths. Circulating tumor cells (CTCs) originate from a primary tumor and initiate a metastasis cascade that ultimately results in metastatic tumors appearing at distal sites. See Sun et al. (2011) *Circulating tumor cells: advances in detection methods, biological issues, and clinical relevance*, J. Cancer Res. Clin. Oncol. 137:1151-1173. Several genetic, morphological, immunological and physio-logical tests may be used to identify CTCs. See Id., and Man, et al. (2011) *Currently used markers for CTC isolation—advantages, limitations and impact on cancer prognosis*, J. Clin. Exper. Pathol. 1:1. Because the number of CTCs in peripheral blood even in patients with advanced metastatic disease, is extremely low compared to the number of normal blood cells (one in a billion), positive selection is a commonly used method for enumeration and isolation of CTCs. CTCs may be captured by using an antibody directed against the epithelial cell adhesion molecule (EpCAM) expressed within the cell membrane of many CTCs. Following selection, the CTCs are ultimately identified by immunostaining using a combination of reagents targeting live cells, leukocyte-specific markers and tumor-specific markers. For example, the FDA-approved CELLSEARCH® CTC test (Veridex, LLC, Raritan, N.J.) detects CTCs using anti-EpCAM monoclonal antibodies poised on paramagnetic beads, followed by CTC identification using DAPI, cytokeratins (CK) and CD45. See Hayes, D. F. and Smerage, J. (2008) *Is there a role for circulating tumor cells in the management of breast cancer?* Clin. Cancer Res., 14:3646-3650; Cristofanilli, M., et al. (2004) *Circulating tumor cells, disease progression, and survival in mestatic breast cancer*. N. Engl. J. Med., 351:781-791. However, reports have suggested that this approach does not capture cells with low or no expression of EpCAM; and the assay shows poor sensitivity and specificity for metastatic cases. See Lu, J. et al. (2010) *Isolation of circulating epithelial and tumor progenitor cells with an invasive phenotype from breast cancer patients*. Intl. J. of Cancer, 126:669-683; Sieuwerts, A. M. et al. (2009) *Anti-epithelial adhesion molecule antibodies and the detection of circulating normal-like breast tumor cells*. J. Natl Cancer Inst, 101:61-66. However, cells with low or no EpCAM expression are also likely to be highly clinically significant. It has been suggested that tumor cells expressing invasive phenotypes down-regulate and lose their epithelial antigens (including EpCAM) in a process called the epithelial-to-mesenchymal transition (EMT). Mego, M. et al. (2010) *Molecular mechanisms of metastasis in breast cancer-clinical applications*. Nat. Rev. Clin. Oncol., 7:693-701; Brabletz, T. et al. (2005) *Invasion and metastasis in colorectal cancer: Epithelial-mesenchymal transition, mesenchymal-epithelial transition, stem cells and Beta-catenin*. Cell Tissues Organs, 179:56-65; Raimondi, C. et al. (2011) *Epithelial-mesenchymal transition and stemness features in circulating tumor cells from breast cancer patients*. Breast Cancer Res, 130:449-455. It has also been suggested that CTCs contain sub-populations with a continuum of phenotypes besides the epithelial one. Therefore, attempts to capture all CTC sub-populations (especially invasive ones that have little if any EpCAM expression) by targeting EpCAM alone may be ineffectual. Sabile, A. et al. (1999) *Efficiency of Ber-EP4 antibody for isolating circulating epithelial tumor cells before RT-PCR detection*. Am. J. Clin. Pathol., 112:171-178; Thurm, H., et al. (2003) *Rare expression of epithelial cell adhesion molecule on residual micrometastatic breast cancer cells after adjuvant chemotherapy*. Clin. Cancer Res., 9:2598-2604. This is further substantiated by the observation that one gram of an epithelial-based tumor can release up to $10^6$ cells per day. Butler, T. P. et al. (1975) *Quantitation of cell shedding into efferent blood of mammary adenocarcinoma*. Cancer Res., 35, 512-516. While clearly not all of these cells possess the ability to initiate metastasis, some rare and elusive sub-populations do.

It may be possible to select CTC sub-populations using a combination of antibodies, e.g., CD45 antibody combined with antibodies for various tumor makers, e.g., HER2 or estrogen receptor. Exemplary tests are offered by BioCept, Inc. (San Diego, Calif.). However, the antibody cocktails typically used in such tests are generated using immortalized cells lines that may not truly recapitulate the continuum of changes occurring in CTCs released from patient tumors. Pecot, C. V. et al. (2011) *A novel platform for detection of CK+ and CK− CTCs*. Cancer Discovery, 1(7):580-586. Accordingly, there is a need for a method able to effectively detect and target rare invasive sub-populations of CTCs present in patient samples.

SUMMARY OF THE INVENTION

In one embodiment, the invention is a method of capturing circulating tumor cells from a sample comprising contacting the sample with a mammalian seprase-targeting affinity reagent, optionally immobilized on a surface of a solid support. In variations of this embodiment, the seprase-targeting affinity reagent is a competitive or a non-competitive inhibitor of seprase, an antibody, a nucleic acid aptamer or a peptide aptamer or a peptide ligand of seprase such as e.g., Ac-Gly-prolineboronic acid (Ac-Gly-BoroPro) or proline diphenyl phosphonate (Gly-ProP(OPh)$_2$). The solid support carrying the seprase-targeting affinity reagent may be a part of a microfluidic device. This may further comprise a step of releasing the captured circulating tumor cells by addition of excess of soluble seprase-binding agent or an avidin compound or by photocleavage or by enzymatic degradation of a bi-functional linker that serves to attach a circulating tumor cell affinity reagent to a solid surface.

In some embodiments, the method further comprises a step of detecting one or more of the following biomarkers: EpCAM, CD146, CK5, CK7, CK18, CK19, CD44, Cd44v6, EphB4, FAP (seprase), IGF-1R, BCL2, HER2, HER3, CA19-9, CEA, CD133, MUC1, N-cadherin, Survivin, EGFR, KRAS, BRAF, p53, Pi3KCA, PTEN, KRT19, CD34, CD24, ACT2, VIM, NANOG, CXCR4 and TWIST1 in the captured cells In another embodiment, the invention is a method of detecting the presence of a malignant tumor in a patient by capturing circulating tumor cells from a patient's sample using a mammalian seprase-targeting affinity reagent. The patient's sample may comprise whole blood, body fluid, any cell-containing blood fraction, a fragmented tumor, a tumor cell suspension, or a cell culture established from a patient's sample, or the culture supernatant, or a xenograft established from a patient's tumor.

In yet another embodiment, the invention is a method of assessing a risk of developing a metastatic tumor in a patient carrying or having carried a tumor by capturing circulating tumor cells from a patient's sample using a mammalian seprase-targeting affinity reagent. The patient's sample may comprise whole blood, body fluid, any cell-containing blood fraction, a fragmented tumor, a tumor cell suspension, or a cell culture established from a patient's sample, or the culture supernatant or a xenograft established from a patient's tumor. In variations of this embodiment, the method further comprises a step of detecting one or more of the following biomarkers: EpCAM, CD146, CK5, CK7, CK18, CK19, CD44, Cd44v6, EphB4, IGF-1R, BCL2, HER2, HER3, CA19-9, CEA, CD133, MUC1, N-cadherin, Survivin, EGFR, KRAS, BRAF, p53, Pi3KCA, PTEN, KRT19, CD34, CD24, ACT2, VIM, NANOG, CXCR4 and TWIST1 in the captured cells.

In yet another embodiment, the invention is a microfluidic device for capturing or isolating selected cells from a liquid comprising one or more modules with a plurality of parallel channels, said channels connected to a common input and to a common output, at least part of the inner surface of said channels are covalently linked to capture elements specific for mammalian seprase protein. In variations of this embodiment, the capture elements may be monoclonal antibodies specific for the mammalian seprase protein, nucleic acid aptamer molecules or peptide aptamer molecules or molecules of a peptide ligand of seprase. In variations of this embodiment, the device contains additional containing capture elements specific for mammalian EpCAM protein or mammalian CD146 protein. In further variations of this embodiment, the device further comprises at least one module for analysis of isolated cells.

DETAILED DESCRIPTION OF THE INVENTION

Definitions

To facilitate the understanding of this disclosure, the following definitions of the terms used herein are provided.

The terms "affinity reagent" refers to a reagent capable of specific binding to its target as defined herein.

The term "bioreactor" refers to a device that supports a biologically active environment wherein cells or tissues can be grown ex vivo.

The term "binding," and "specific binding" are used interchangeably to refer to the ability of a reagent to selectively bind its target. Typically, specificity is characterized by a dissociation constant of $10^4 M^{-1}$ to $10^{12} M^{-1}$. Empirical methods using appropriate controls may be employed to distinguish specific and non-specific binding in a particular case.

The term "cancer cells" and "tumor cells" are used interchangeably to refer to cells derived from a cancer or a tumor, or from a tumor cell line or a tumor cell culture.

The term "metastatic cells" or "metastatic tumor cells" refers to the cells that have the ability to produce a metastasis or are already a part of a metastatic tumor.

The term "circulating tumor cells" or "CTCs" refers to tumor cells found in circulation of a patient having a tumor. This term typically does not include hematological tumors where the majority of the tumor is found in circulation.

The term "matrix" or "solid support" are used interchangeably to refer to solid material present e.g. in a vessel or chamber. Solid support may be decorated with reagents, e.g. affinity reagents. Solid support may also support adhesion of cells via biological, chemical or electrostatic forces and processes.

The term "primary tumor" refers to a tumor growing at the site of the cancer origin.

The term "metastatic tumor" refers to a secondary tumor growing at the site different from the site of the cancer origin.

The term "cell line" refers to a population of cells that through cell culture, has acquired the ability to proliferate indefinitely in vitro.

The term "primary cell culture" refers to a cell culture established from an organism in the course of a study. A primary cell culture may or may not give rise to a cell line.

The term "established cell line" refers to a cell line propagated in vitro multiple times prior to a study.

The term "biomarker" refers to a biological marker characterizing a phenotype. A biomarker typically includes a gene or a gene product. Depending on the gene, "detecting a biomarker" may include detecting altered gene expression, epigenetic modifications, germ-line or somatic mutations, etc. In case of a gene product, "detecting a biomarker" may mean detecting the presence, quantity or change in quantity of a cell surface marker, a soluble compound such as cytokine, etc. "Detecting a biomarker" may also include detecting gene expression (mRNA or protein) or a metabolite reflective of a gene's expression or activity.

The term "targeting reagent" is synonymous with "affinity reagent" and refers to a reagent capable of targeting a molecule via specific binding thereto.

The term "tumor biomarker" or "cancer biomarker" refers to a biomarker characteristic of a tumor or cancer but not normal tissue.

The gene and protein name "seprase" is used interchangeably with the synonyms "Fibroblast Activation Protein alpha," "FAPα," and "FAP," to designate the same gene or its protein product.

The present invention comprises a method of enriching sub-populations of CTCs that have lost some or all characteristics of their epithelial phenotype and display more invasive behavior. The invention utilizes seprase as a target molecule for capture and enrichment of CTCs for further characterization. Seprase protein is described in U.S. Pat. No. 5,767,242. Seprase, also known as Fibroblast Activation Protein alpha (FAPα) and DPP-5, is a protease (gelatinase) that has been shown to be involved in degradation of the extracellular matrix (ECM) and enhancing tumor growth and proliferation. Seprase is a membrane-tethered protein existing as a 170 kDa homodimer comprised of two N-glycosolated 97 kDa subunits. Seprase also exists in a soluble form that bears the name Antiplasmin Cleaving Enzyme (APCE), Lee, K., et al. (2006) *Antiplasmin-cleaving enzyme is a soluble form of fibroblast activation protein*, Blood, 107:1397-1404.

Structurally, seprase contains a large C-terminal extracellular domain, a hydrophobic transmembrane domain and a short cytoplasmic tail. Interestingly, the distribution of seprase on the surface of tumor cells is not uniform: it is mostly present on the invading front of human malignant tumor cells, especially within the invadopodia, membrane protrusions that can associate with the extracellular matrix. Edosada, C. Y., et al. (2006) *Selective Inhibition of Fibroblast Activation Protein Protease Based on Dipeptide Substrate Specificity*. J. Biol. Chem., 281: 7437-7444; Mori Y., et al. (2004) *The expression of a type II transmembrane serine protease (Seprase) in human gastric carcinoma*. Oncology, 67:411-419; O'Brien, P., et al. (2008) *Seprase: an overview of an important matrix serine protease*. Biochim Biophys Acta, 1784:1130-1145; Monsky, M. J. et al. (1994) *A potential marker protease of invasiveness, seprase, is localized on invadopodia of human malignant melanoma cells*. Cancer Research, 54:5702-5710; Mueller, S. C., et al. (1999) *A Novel Protease-docking Function of Integrin at Invadopodia*. J. Biol. Chem., 274: 24947-24952.

Seprase has been found to be overexpressed on cell surfaces in >90% of human epithelial cancers, but absent in non-cancerous tissues and fibroblasts of benign epithelial tumors. Aertgeerts, K., et al. (2005) *Structural and Kinetic Analysis of the Substrate Specificity of Human Fibroblast Activation Protein α*. J. Biol. Chem., 280:19441-19444. A study of isolated CTCs showed that cell populations captured by an anti-EpCAM antibody do not express seprase; while among cell populations captured using their affinity to cell adhesion matrix (CAM) proteins, only some express seprase. See Lu, J., et al. (2010) *Isolation of circulating epithelial and tumor progenitor cells with an invasive phenotype from breast cancer patients*. Intl J. Cancer, 126: 669-683. It is known that during the metastatic process, proteolytic degradation of the extracellular matrix (ECM) occurs; and furthermore, some sub-populations of invasive CTCs with avidity towards cell adhesion matrix (CAM) overexpress seprase. See Id.

The present invention is a method of capturing CTCs using affinity reagents specific for seprase. In some embodiments, CTCs are isolated from a patients' sample that may be derived from whole blood, body fluid, any cell-containing blood fraction, a fragmented tumor, a tumor cell suspension, or a cell culture established from a patient's sample, or the culture supernatant. In other embodiments, CTCs are isolated from an established cell line culture or culture supernatant or from an experimental animal, e.g. from an animal carrying a xenograft tumor. In some embodiments, the method includes a dual-selection configuration: following the seprase selection, epithelial-like CTCs are further selected using affinity reagents specific for EpCAM. The order of selection may also be reversed and EpCAM used as the initial selection. In yet another alternative, seprase and EpCAM selection may be applied simultaneously. Alternatively, seprase-positive and EpCAM-positive cells can be isolated or enumerated separately and the ratio of such cells may be obtained. The change in the ratio of seprase-positive and EpCAM-positive cells is indicative of a change in metastatic potential of the cancer.

In some embodiments, the level of seprase expression in a particular normal tissue or corresponding tumor tissue is first assessed. For example, flow cytometry may be used to calculate the percentage of cells in the tumor that express seprase. If the percentage is observed to be low, the concentration or density of the seprase-specific capture reagents in the capture device may be modified to assure optimal kinetics of binding and capture of seprase-expressing CTCs. In the same way, the seprase/EpCAM ratio in a particular In some embodiments, in addition to or instead of EpCAM, other molecules associated with epithelial-mesenchymal transition may be used for selection. See e.g., Zeng, Q., et al. (2012) *CD146, an epithelial-mesenchymal transition inducer, is associated with triple-negative breast cancer*. PNAS 109(4):1127-32.

In some embodiments, the seprase-expressing cell populations including CTCs, are captured using seprase-specific antibodies. Seprase-specific antibodies are available from commercial sources (e.g., Antibody Resource, Cambridgeshire, UK). Alternatively, seprase-specific antibodies may be generated de novo using methods known in the art. See e.g., Howard and Kaser, Eds., (2006) *Making and Using Antibodies: A Practical Handbook*, CRC Press; Harlow and Lane (1988) *Antibodies: A Laboratory Manual*, CSHL Press. Optionally, a secondary selection may be accomplished using anti-EpCAM antibodies. EpCAM specific antibodies are widely available from multiple suppliers, e.g. OriGene Tech., Rockville, Md. Further selection may be employed with additional antibodies e.g., antibodies specific for CD146 (American Research Products, Inc., Waltham, Mass.).

In another embodiment, the capturing molecule is a seprase ligand or an inhibitor of seprase. In some embodiments, the ligand or the inhibitor is a peptide. Exemplary peptides are Ac-Gly-prolineboronic acid (Ac-Gly-BoroPro) and proline diphenyl phosphonate (Gly-ProP(OPh)$_2$), octopeptides and cyclical octopeptides described in U.S. Pat. No. 7,374,898. These ligands have been extensively characterized and show favorable affinity to seprase. See Edosada, C. Y., et al. (2006) *Selective Inhibition of Fibroblast Activation Protein Protease Based on Dipeptide Substrate Specificity*. J. Biol. Chem., 281:7437-7444; and Aertgeerts, K., et al. (2005) *Structural and Kinetic Analysis of the Substrate Specificity of Human Fibroblast Activation Protein α*. J. Biol. Chem., 280:19441-19444. Other peptide ligands of seprase can be generated in vitro by one skilled in the art using e.g. peptide selection methods described in Bartoli, L., et al. (2007) *A computational approach for detecting peptidases and their specific inhibitors at the genome level*. BMC Bioinformatics March 8; 8 Suppl 1:S3; or Yagi, Y., et al. (2007) *In silico panning for a non-competitive peptide inhibitor*. BMC Bioinformatics, January 12; 8:11.

In yet another embodiment, the capturing molecule is a peptide or a nucleic acid aptamer. Such aptamers can be selected from oligonucleotide or peptide libraries by any method known in the art. The nucleic acid aptamers may be selected via SELEX (Systematic Evolution of Ligands by Exponential Enrichment), see Oliphant A R, et al. (1989). *Defining the sequence specificity of DNA-binding proteins by selecting binding sites from random-sequence oligonucleotides: analysis of yeast GCN4 proteins*. Mol. Cell Biol. 9:2944-2949. Peptide aptamers may be selected using the yeast or bacterial two-hybrid system, see Fields, S., Song, O. (1989). *A novel genetic system to detect protein-protein interactions* Nature 340 (6230): 245-6; Joung, J., et al. (2000) *A bacterial two-hybrid selection system for studying protein-DNA and protein-protein interactions*, Proc. Natl. Acad. Sci. U.S.A. 97 (13): 7382-7.

In some embodiments, the invention is a device capable of capturing CTCs from a patient's sample. The device comprises seprase-targeting affinity reagents immobilized on a solid surface. The solid surface may comprise polymer-based matrices that are decorated with affinity reagents targeting seprase and optionally, in addition or in parallel, EpCAMIn some embodiments, the seprase-expressing cell populations including CTCs are captured in a device containing surfaces decorated with anti-seprase antibodies. Optionally, a secondary selection may be used wherein the device contains surfaces decorated with anti-EpCAM or anti-CD146 antibodies or any additional antibody of interest. In some embodiments, the affinity reagents (e.g., seprase-specific and EpCAM-specific antibodies) may be combined to form a mixed monolayer, yet in other embodiments the seprase-specific and EpCAM-specific antibodies are located in consecutive beds (positioned in either order). In other embodiments, the seprase-expressing CTCs are captured in a device containing surfaces decorated with peptide ligands of seprase such as for example, Ac-Gly-prolineboronic acid (Ac-Gly-BoroPro) and proline diphenyl phosphonate (Gly-ProP(OPh)$_2$). Other suitable peptides may be selected according to in vitro and in silico peptide selection methods known in the art. In yet another embodiment, the seprase-expressing CTCs are captured using peptide or nucleic acid aptamers specific for seprase. In some embodiments, the device is a microfluidic device that can be interfaced to a fluidic motherboard incorporated into a functional system with an automated workflow. In such a device, one or more CTC selection modules are configured on a fluidic motherboard so that once the cells are released they can be further enriched and subjected to immunological and molecular profiling.

Typically, the microfluidic device is suitable to accommodate and process large volumes of sample necessary to detect CTCs occurring in patient's sample at an extremely low rate. To that end, the device may be equipped with multiple channels accommodating linear flow of the sample. The linear flow velocity optimal for maximum recovery of seprase or EpCAM-expressing cells may be experimentally determined by one skilled in the art of microfluidics.

In some embodiments, the analytical cell capture device is constructed in a manner that maximizes attachment of the seprase-expressing cells to the surface of the device. For example, the surface may be roughened using UV light. Furthermore, in some embodiments, the surface of the device may be nanotextured to create microscopic structures that facilitate the capture and retention of CTCs. For example, the surface may be treated to create nanopillars as described e.g., in Wang, S., et al. (2009) *Three-dimensional nanostructured substrates toward efficient capture of circulating tumor cells*. Angewandte Chemie Int'l. Edition, 48:8970-8973. An exemplary device generally suitable for selection of circulating tumor cells is described e.g. in the International Application PCT/US2009/043697 filed on May 13, 2009.

Figure 1:
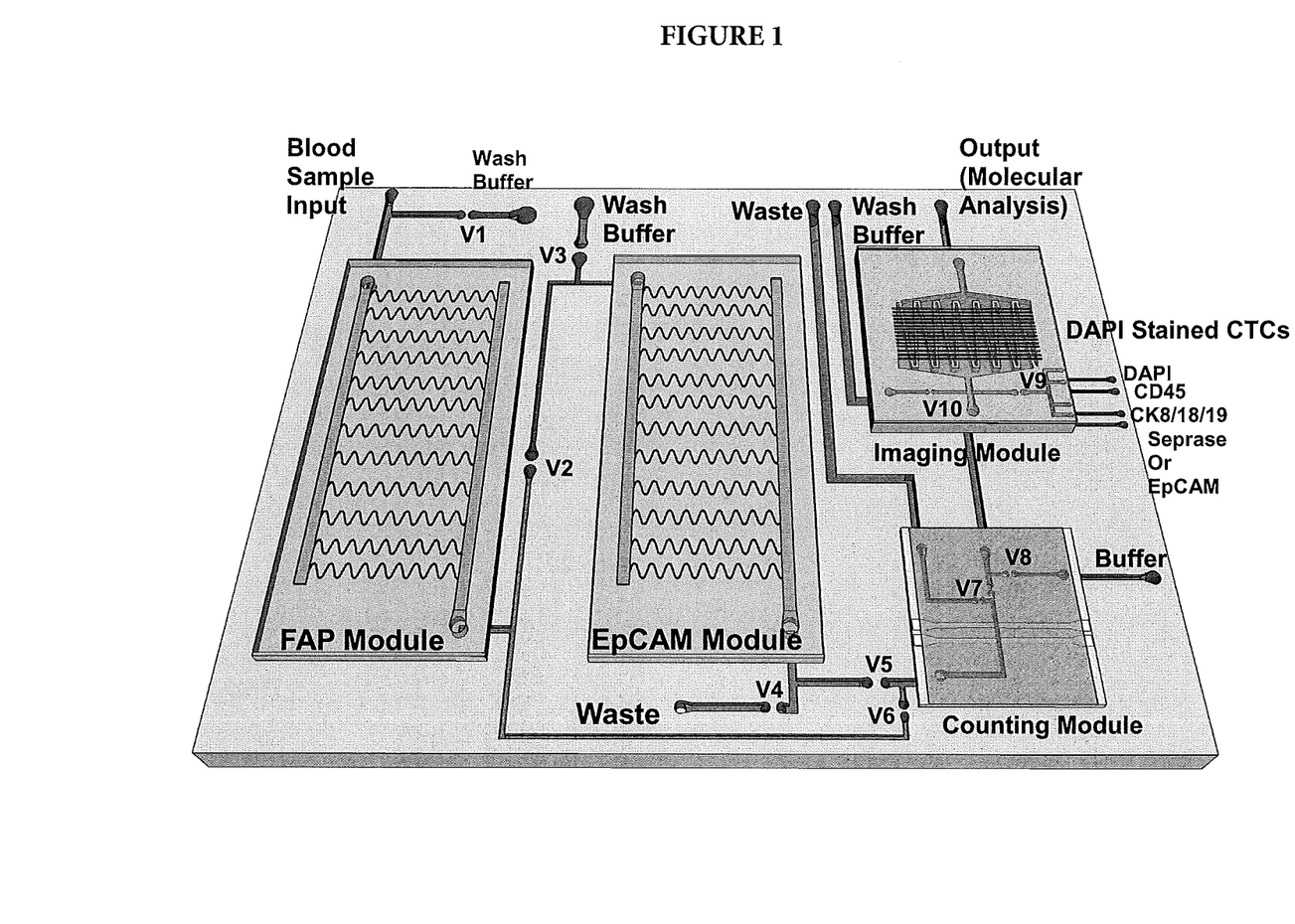
FIG. 1 is a diagram of an exemplary microfluidic device for practicing the invention.

An exemplary device is shown in FIG. 1. The device in FIG. 1 contains multiple capture modules, each enclosing sinusoid-shaped channels containing an inner surface decorated with affinity reagents used for selection. The device in FIG. 1 has two capture modules: one for seprase and one for EpCAM arranged in a serial configuration (output of one module serves as the input to the second module). A skilled practitioner would appreciate that additional modules can be added. According to the invention, the order of affinity selection steps can also be reversed. In yet another alternative, the selection modules may be operated in a parallel configuration in which the input sample is split to run in each CTC selection module simultaneously. In yet another alternative, a single module with a mixture of two or more antibodies may be used. The device has containers for wash buffers, waste collection and other reagents. The device possesses multiple valves (V) to direct flow. After selection, the cells are directed to the optional counting module and an optional staining module. Various cell counting devices and methods are known in the art and may be employed by a skilled practitioner. For example, the counting module may contain pairs of electrodes so that cells can be identified and enumerated using single cell impedance. See T. Sun and H. Morgan (2010) *Single-Cell Microfluidic Impedance Cytometry: A Review*, Microfluid Nanofluid, 8:423-443 and citations therein. The staining module is configured to receive various staining reagents, e.g. dyes (DAPI) and labeled antibodies (specific for cytokeratins (CK), CD45 and any other targets of interest). The device output delivers selected cells for further processing, e.g. molecular analysis according to the invention.

In some embodiments, it may be desirable to release CTC-containing cell sub-populations captured using the seprase-targeting affinity reagent attached to a solid surface and further, optionally the EpCAM-targeting affinity reagent attached to a solid surface for further analysis. The release can be accomplished either by cleaving the bond tethering the affinity reagent to the solid matrix, or by displacing the captured cells from the affinity reagent.

In one embodiment, the method of the invention utilizes cleavable bi-functional linkers for the capturing antibodies, e.g. photo-cleavable or chemical groups contained within the bi-functional linkers to enable release of the captured cells. Several photo-cleavable linkers are available to one skilled in the art, see e.g Kanoh, N., et al. (2010) *Cleavable linker for photo-cross-linked small-molecule affinity matrix*, Bioconjug. Chem. 21:182-186 and citations therein. The use of photocleavable linkers are ideal candidates for clinical applications, where the cell selection module is used once and then discarded. These bi-functional linkers can consist of different lengths and composition, such as single-stranded oligonucleotides that contain the photocleavable residue or an abasic site that can be cleaved enzymatically.

In another embodiment, the invention utilizes an avidin compound, e.g. avidin, streptavidin, nitroavidin or neutravidin, interacting with a biotinylated capturing antibody to enable capture and release of cells. The avidin compound dissociates from the biotin part of the biotinylated antibody upon a change in pH of the solution from neutral to alkaline in the case of nitroavidin. The advantage of this embodiment is the ability to regenerate the binding surface.

In yet another embodiment, where cells are captured using peptide inhibitors, ligands or other binding partners to enable release of captured cells, the cells are made to dissociate from the matrix by adding excess of the binding agent in soluble form.

In yet another embodiment, with nucleic acid aptamers serving as the affinity reagent, excess of the soluble form of a complement to the affinity aptamer can be used to release the selected CTC. Following heat denaturation, such aptamer-decorated capture surface may be easily regenerated.

In some embodiments, the captured cell sub-population that includes CTCs is released from the affinity reagent and subjected to further analysis. In some embodiments, the cells are subjected to microscopic examination after staining for example, with hematoxylin and eosin (H&E) or other differential stains, e.g., PROTOCOL® HEMA 3 staining. All cells may be stained with the fluorescent nucleic acid-binding dye, such as Hoechst 33342 or DAPI to aid in differentiating cells from cellular debris. Cells exhibiting positive staining with the various markers described below may be identified as CTCs, counted and further characterized.

Several biomarkers as well as morphological, immunological and physiological tests or combinations thereof may be used to identify CTCs among the cells captured using the method of the present invention. See e.g. Sun et al. (2011), *Circulating tumor cells: advances in detection methods, biological issues, and clinical relevance*, J. Cancer Res. Clin. Oncol. 137:1151-1173; Man, et al. (2011); *Currently used markers for CTC isolation—advantages, limitations and impact on cancer prognosis*, J. Clin. Exper. Pathol. 1:1. For example, CTCs may be identified by their ability to adhere to cell adhesion molecules (CAM), as well as by the presence of certain specific biomarkers including EpCAM, cytokeratins (CK) 5, 7, 18 and 19, CD44v6 or N-cadherin. Depending on the tumor of origin, CTCs may also be identified based on the presence of tumor-specific biomarkers including EpCAM, CD146, CK5, CK7, CK18, CK19, CD44, Cd44v6, EphB4, FAP (seprase), IGF-1R, BCL2, HER2, HER3, CA19-9, CEA, CD133, MUC1, N-cadherin, Survivin, EGFR, KRAS, BRAF, p53, Pi3KCA, PTEN, KRT19, CD34, CD24, ACT2, VIM, NANOG, CXCR4 and TWIST1.

For example, CTCs originating from the pancreas would exhibit positive staining with standard epithelial markers and human pancreatic tumor markers (EpCAM and CA19-9). In some embodiments of the invention, CTC are identified using commercially available assays, e.g. VITA-ASSAY™ AR16 platform (Vitatex, Inc., Stony Brook, N.Y.).

In another embodiment, the invention is a method of detecting the presence of a malignant tumor or assessing metastatic potential of an existing or excised tumor in a patient by detecting seprase-expressing cells in a patient's sample. The sample may comprise whole blood, body fluid, any cell-containing blood fraction, a fragmented tumor, a tumor cell suspension, or a cell culture established from a patient's sample, or the culture supernatant.

In this embodiment, the captured seprase-expressing cells may be further characterized as CTCs and assessed for their numbers and gene expression profile comprising e.g., one or more of the biomarkers ACT2, IGF-1R, BCL2, HER2, EphB4, CA19-9, CEA, CD24, CD44, CD133, CD146, CXCR4, TWIST1, VIM, NANOG, KRT19, MUC1, Survivin, EGFR, KRAS, BRAF, p53, Pi3KCA and PTEN.

In another embodiment, the invention is a method of comparing seprase expression to the EpCAM expression in the tumor or CTCs derived from the tumor using the method of the present invention. The ratio of seprase expressing CTCs to EpCAM expressing CTCs may be used to determine metastatic potential of the tumor.

In yet another embodiment, the invention is a method of determining prognosis for a patient having a tumor, the method comprising determining the metastatic potential of the tumor by assessing the ratio of seprase expressing CTCs to EpCAM expressing CTCs wherein the increase in the ratio indicates increase in metastatic potential of the tumor and thus poor prognosis for the patient. The increase in the ratio of seprase expressing CTCs to EpCAM expressing CTCs may be detected by comparing the experimentally determined ratio to documented ratios of seprase expressing CTCs to EpCAM expressing CTCs for the particular tumor type. Alternatively, the ratio of seprase expressing CTCs to EpCAM expressing CTCs may be repeatedly assessed (monitored) for the particular patient so that an increase in the ratio could be detected. According to the method, the prognosis may be fowled for any malignant solid tumor known to have metastatic potential, including without limitation, lung cancer (e.g., non-small cell lung cancer (NSCLC)), bone cancer, pancreatic cancer, cancer of the head or neck, melanoma, uterine cancer, ovarian cancer, cervical cancer, colorectal cancer, gastric cancer, breast cancer, endometrial cancer, thyroid cancer, prostate cancer, bladder cancer, kidney cancer (e.g., renal cell carcinoma), liver cancer (e.g., hepatocellular carcinoma), and cancers of the central nervous system (CNS), (e.g., glioma, glioblastoma multiforme or astrocytoma).

EXAMPLES

Example 1

Selection of Seprase(+) and EpCAM(+) Circulating Tumor Cells (CTCs) from the Peripheral Blood of Pancreatic Cancer Patients The following clinical measurements were secured from an approved IRB (University of North Carolina, Chapel Hill, Lineberger Cancer Center). These measurements are intended to illustrate embodiments of the present invention and not intended to limit the scope of the invention. The current invention is intended to include all adenocarcinomas or solid tumors.

Materials & Methods

The CTC microchips used for selection of seprase and EpCAM positive cells were fabricated in a thermoplastic (cyclic olefin co-polymer, COC or poly(methylmethacrylate), PMMA). The CTC microchips consisted of an architecture comprised of 50 sinusoidally-shaped channels that emanated from a common input and converged into a common output (see Adams et al., *Highly Efficient Circulating Tumor Cell Isolation form Whole Blood and Label-Free Enumeration Using Polymer-based Microfluidics with an Integrated Conductivity Sensor*, Journal of the American Chemical Society, 139 (2008) 8633-8641). The sinusoidal channels were 30 μm wide and 150 μm deep.

Polymer substrates and cover plates (0.5 mm thickness) were purchased from Good Fellow (Berwyn, Pa.). Platinum wires were purchased from Alfa Aesar (Boston, Mass.). Polyimide-coated fused silica capillaries were purchased from Polymicro Technologies (Phoenix, Ariz.). Chemicals used for the COC surface cleaning and modification included reagent grade isopropyl alcohol, 1-ethyl-3-[3-dimethylaminopropyl] carbodiimide hydrochloride (EDC), N-hydroxysuccinimide (NHS), fetal bovine serum and 2-(4-morpholino)-ethane sulfonic acid (MES) and these were purchased from Sigma-Aldrich (St. Louis, Mo.). Monoclonal anti-EpCAM antibody and the anti-seprase antibody were obtained from R & D Systems (Minneapolis, Minn.).

The CTC microchips were manufactured via micro-replication from a metal master. Microstructures of the metal master were milled onto the surface of a brass plate with a high-precision micromilling machine (KERN MMP 2522, KERN Micro- and Feinwerktechnik GmbH & Co.KG; Germany) following previously published procedures (Huper et al., *Evaluation of Micromilled Metal Mold Masters for the Replication of Microchip Electrophoresis Devices*, Microfluidics and Nanofluidics, (2007) 3: 1-11). The micromilling machine was fitted with a laser measuring system (LaserControl NT, Blum-Novotest GmbH, Germany) for automatic determination of tool length and radius, and an optical microscope (Zoom 6000, Navitar, Inc. Rochester, N.Y.) for monitoring the milling process. Micromilling was carried out at 40,000 rpm. Feed rates were dependent on the size of the milling tool and were typically in the range of 200 mm/min for a 500 μm milling bit, 100-150 mm/min for the 200 μm bit, 50-75 mm/min for the 100 μm bit and 10-20 mm/min for a 50 μm bit. A typical milling cycle consisted of a pre-cut of the entire surface with a 500 μm milling bit to ensure parallelism between both faces of the brass plate and uniform height of the final milled microstructures over the entire pattern, a rough milling of the microstructures using either a 500 or 200 μm milling bit, and a finishing cut with a smaller diameter milling bit. In the final step of mold master fabrication, burrs were removed by mechanical polishing. Polishing was performed by hand on a 3 μm grain-size polishing paper (Fibrmet Discs—PSA, Buehler, Lake Bluff, Ill.) followed by polishing on a polypropylene cloth (Engis, Wheeling, Ill.) with a 1 μm diamond suspension (Metadi Diamond Suspension, Buehler).

Following UV modification of the polymer substrates and cover plates, the physicochemical properties of the surface were effectively altered resulting in a moderate reduction of the glass transition temperature ($T_g$) at the cover plate-substrate interface. Thermal fusion bonding was carried out in a gas chromatographic (GC) oven (Varian 3400, Palo Alto, Calif.) using the polymer cover plate and the open-faced, hot embossed polymer substrate. The substrate and cover plate were aligned and clamped together between two borosilicate glass plates and the assembly placed into the temperature programmable oven of the GC, where the temperature was increased from 50° C. to 150° C. at a rate of 20° C./min. The temperature was held at 150° C. for 15 min before cooling to room temperature.

Regio-specific ultraviolet (UV) modification of the polymer substrate and cover plate was performed through an aluminum photomask to facilitate the formation of the carboxylated scaffold for directed antibody tethering exclusively within the cell selection beds of the CTC microchips. Before final assembly via thermal fusion bonding, the cover plate and substrate were locally irradiated at 254 nm with 15 mW cm$^{-2}$ fluence for 10 min using a UV exposure station (ABM, Inc., San Jose, Calif.).

Antibody immobilization was performed using a two-step process. Initially, the UV-modified CTC device, following thermal assembly, was loaded with a solution containing 4.0 mg/mL of 1-ethyl-3-[3-dimethylaminopropyl]carbodiimide hydrochloride (EDC), 6.0 mg/mL of N-hydroxysuccinimide (NHS) in 150 mM 2-(4-morpholino)-ethane sulfonic acid at pH=6 (MES, Fisher Biotech, Fair Lawn, N.J.) and buffered saline (Sigma-Aldrich, St. Louis, Mo.) for 1.0 h to form a succinimidyl ester intermediate. The EDC/NHS solution was then hydrodynamically replaced with a 1.0 mg/mL monoclonal antibody for EpCAM or the monoclonal anti-seprase antibody (R&D Systems Inc., Minneapolis, Minn.) solution contained in 150 mM PBS at pH=7.4 (Sigma-Aldrich, St Louis, Mo.) and allowed to react for 4 h after which the CTC microchips were rinsed with a solution of PBS (pH=7.4) to remove any non-specifically bound antibodies.

A PHD2000 syringe pump (Harvard Apparatus, Holliston, Mass.) was used to hydrodynamically process samples using the CTC microchips. In order to interface the microchip to the pump, a luer lock syringe (Hamilton, Reno, Nev.) was fitted with a luer-to-capillary adapter (InnovaQuartz, Phoenix, Ariz.). The syringe pump was programmed to generate the appropriate volume flow rate to evaluate CTC cell capture efficiency and post-capture cell retention. The linear velocities were calculated from the cross-sectional area of the respective HTMSU capture channels and the programmed volume flow rate. The dual-selection process was carried out by interfacing the seprase CTC microchip directly to the syringe pump. The output of the seprase chip was then directed into the EpCAM microchip. Thus, the blood sample was processed in a single assay using both microchips arranged serially.

Blood samples from consenting pancreatic cancer patients were collected into an EDTA tube with an approximate 10 ml total volume. Once the samples were collected, they were immediately processed using the CTC microchips. Typically 3 ml of whole blood was removed from the EDTA tube and placed into a sterilized plastic syringe and affixed to a syringe pump and connected to the CTC microchip. The blood sample was processed at a volume flow rate of ~150 μl/min, requiring 20 min to process an input volume of 3 ml. Following blood processing, the microchip was washed with an isotonic buffer (PBS, 1.5 ml).

Selected cells (those remaining on the surface following PBS washing of the microchip) were stained directly using DAPI (nuclear stain), fluorescein-labeled antibodies directed against CD45, anti-cytokeratin (8,18,19) antibodies labeled with phycoerythrin (PE) and anti-EpCAM antibodies labeled with Cy7 (for the seprase+ chip) or anti-seprase antibodies labeled with Cy7 (for the EpCAM+ chip). Following staining and washing, the chips were imaged on a Zeiss Axiovert 200M using a 40× microscope objective and an EMCCD camera. We found that >95% of the seprase+ cells did not express visible levels of EpCAM as discerned from the on-chip staining using anti-EpCAM antibodies labeled with Cy7 fluorescent dye. EpCAM+ cells were also immunophenotyped as well using anti-seprase antibodies labeled with Cy7 with similar results secured (>95% EpCAM+ cells were found to not express seprase).

Results from several clinical samples are shown in Table 1. In Table 1, the column "Pathology" lists the stage of disease at the time the sample was taken. "Affinity Ab" indicates the antibody used to capture CTCs from the sample. Cell numbers are given per 7.5 ml of blood. Purity is calculated as a ratio of CTCs (Seprase+ or EpCAM+) to total number of cells selected (WBCs (CD45+)+CTCs+triple stained cells−those cells (CD45+, DAPI+ and CK+)). The samples analyzed included samples from metastatic patients and those with localized disease. In addition, a single patient was tracked with localized disease both before and 3 weeks post-surgery (resection of diseased tissue). The ratio of seprase+ CTCs to EpCAM+ CTCs is also shown as a function of pathology.

TABLE 1

Seprase and EpCAM-selected CTCs

| Pathology | Affinity Ab | CTCs (per 7.5 ml) | WBCs (per 7.5 ml) | Purity | FAP/ EpCAM Ratio |
|---|---|---|---|---|---|
| Met Pancreatic | FAP | 158 | 11 | 94% | |
| Met Pancreatic | EpCAM | 176 | 13 | 90% | 0.92 |
| Met Pancreatic | FAP | 94 | 21 | 82% | |
| Met Pancreatic | EpCAM | 11 | 15 | 42% | 8.54 |
| Met Pancreatic | FAP | 625 | 10 | 98% | |
| Met Pancreatic | EpCAM | 98 | 13 | 88% | 6.38 |
| Non-Met Pancreatic | FAP | 11 | 7 | 61% | |
| Non-Met Pancreatic | EpCAM | 34 | 5 | 87% | 0.32 |
| Non-Met Pancreatic | FAP | 94 | 19 | 83% | |
| Non-Met Pancreatic | EpCAM | 581 | 28 | 95% | 0.16 |
| Localized Pancreatic (30-days post-OP) | FAP | 73 | 9 | 89% | |
| Localized Pancreatic (30-day post-OP) | EpCAM | 91 | 12 | 88% | 0.80 |
| Localized Pancreatic (resected) | FAP | 237 | — | — | |
| Localized Pancreatic (resected) | EpCAM | 125 | — | — | 1.90 |
| 3 Weeks Post-OP | FAP | 30 | — | — | |
| 3 Weeks Post-OP | EpCAM | 39 | — | — | 0.77 |
| Non-Cancer | FAP | 0 | 8 | — | — |
| Non-Cancer | EpCAM | 1 | 4 | — | — |

Example 2

Determining the Ratio of Seprase(+) and EpCAM(+) CTCs from the Peripheral Blood of Patients with Various Cancers CTC microfluidic chips were fabricated in COC substrates. The chip design consisted of a 26.3×20.5 mm footprint with inlet and outlet leading channels (20.5 mm long, 400 μm wide, and 150 μm deep) connecting a series of 50-curvilinear channels that in concert formed the cell selection bed. FIG. 1 shows the CTC selection chip design. Each curvilinear selection channel was 30.6 mm long, 150 μm deep, and 25 μm wide. The surface area of the CTC selection bed was 596 mm$^2$ (11 mm$^2$/channel) with 45.1 mm$^2$ of that surface area in the lead channels. The chip's total volume was 9.4 μL (138 nL/channel) with 2.5 μL volume for the lead channels.

The depth of these channels increased the throughput as well as provided reduced pressure drop throughout the selection channels, especially when occupied by captured CTCs. On average, the widths of microchannels are only slightly larger than the average CTC diameter (12-20 μm), which maximizes recovery, but much larger than the average leukocyte diameter (7-15 μm). Channel width plays a role in maximizing the probability of cell/wall interactions and allows for achieving high CTC yield but lower probability of interactions with smaller cells. For even smaller cells, such as erythrocytes, the likelihood of approaching the channel wall is very limited due in part to the formation of a marginal cell-free layer.

ENREF 84

Figure 2:
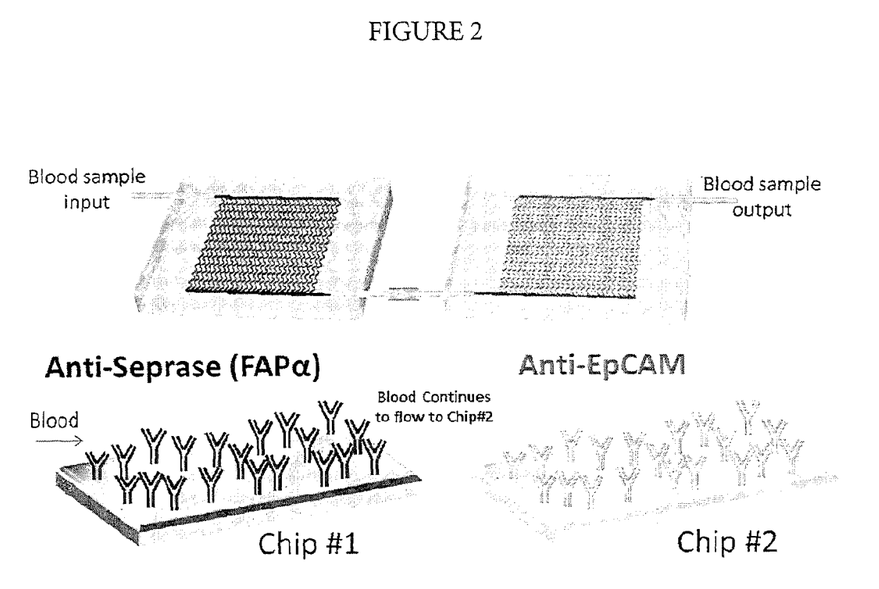
FIG. 2 is a diagram of CTC chips connected in series for isolating both EpCAM and seprase CTCs from blood and the subsequent CTC enumeration.

UV-activated COC chips were modified with anti-human FAPα (MAB3715 R&D), anti-human EpCAM: (MAB960, R&D) as shown in FIG. 2. Ab attachment was performed utilizing the following protocol: activation of UV-COC surface with 20 mg/mL EDC and 2 mg/mL NHS pH 4.8 during 15-20 minutes incubation, followed by emptying channels and replacing with 0.5 mg/mL Ab in PBS pH 7.4 and overnight incubation at 4° C. Before blood processing, the chips were rinsed with 2 mL PBS/0.25% BSA.

Chips were equipped with silica capillaries which were connected to syringe pump at the input of chip#1. The outlet of the chip#1 was connected to the inlet of chip #2 using a glass connector. Cell Capture protocol for the 50-channel COC chip involved infusing whole blood (undiluted and unfixed) through the chips at 25 μL/min (2 mm/s) followed by a chip wash at 55 μL/min (4 mm/s) with 1-2 mL of PBS/BSA solution.

Selected cells were analyzed and identified via immunostaining by: (i) treating with Fc blocker (IgG); (ii) incubation with anti-mouse or anti-human CD45-FITC Abs for 30 min; (iii) cell fixation with 2% PFA; (iv) poration with 0.1% Triton-X100; and (v) incubation with CK8/19-PK Abs and the nuclear dye, DAPI. Images of stained cells were obtained using an Olympus IX71-DSU Spinning Disk Confocal inverted microscope controlled via MetaMorph software that was furnished with 10×, 20×, and 40× dry objectives, a mercury arc lamp illumination source, two cameras (high sensitivity Hamamatsu EMCCD and high resolution Hamamatsu ORCA-03G CCD), and DAPI, FITC, TRITC, and Cy5 filter sets.

TABLE 2

Data Summary for CTCs captured on anti-FAPα and anti-EpCAM Beds from Clinical Samples (normalized to 1 mL).

| Affinity Ab | Metrics | Negative control (n = 5) | Benign Tumor (n = 4) | Operable Localized PDAC, Later Diagnosed as Metastatic (n = 4) | Metastatic PDAC (n = 16) | Metastatic Melanoma (n = 11) | Metastatic CRC (n = 6) |
|---|---|---|---|---|---|---|---|
| FAPα | Avg ± SD | 0.6 ± 0.7 | 3.1 ± 1.3 | 25.5 ± 10.1 | 28.7 ± 23.7 | 33.2 ± 26.5 | 68.1 ± 104.5 |
|  | Median | 0.5 | 3.3 | 22.2 | 22.8 | 21 | 31.3 |
|  | Range | 0-2 | 1.5-3 | 17.5-40 | 4.75-80.0 | 8.2-89.5 | 12.5-280 |
| EpCAM | Avg ± SD | 0.6 ± 0.5 | 2.5 ± 1.5 | 25.0 ± 2.6 | 24.5 ± 18.9 | 73.0 ± 87.6 | 36.6 ± 37.7 |
|  | Median | 0.5 | 2.5 | 23.5 | 20 | 50 | 24.3 |
|  | Range | 0-1.5 | 1-4 | 23.5-28 | 3.5-70.3 | 6.0-310.5 | 12-111 |

Table 2 summarizes data for CTCs captured from clinical samples. Blood samples from patients and healthy donors (negative controls) were either infused on a IgG or FAPα/EpCAM modified CTC chips. The number of cells classified as CTCs per 1 mL of blood is presented. Cells were classified as CTCs using staining (DAPI+; CK+; CD45−). Number of measurements is indicated in brackets.

In all tested blood samples collected from metastatic PDAC, melanoma, and colorectal cancers, CTCs were detected on both affinity beds. In the anti-FAPα bed the highest sensitivity was observed for CTCs collected from colorectal cancer patients' blood. Metastatic melanoma and PDAC showed similar median, but higher average values for melanoma. In the anti-EpCAM bed the highest sensitivity of CTC detection was reported in melanoma, followed by colorectal and PDAC metastatic patients. For all metastatic disease-related CTCs the counts of these cells were significantly different when compared to negative controls and benign tumors.

Blood from 4 patients initially identified/diagnosed as having localized and operable PDAC cancer was analyzed on the day of scheduled surgery (OR) and CTCs were enumerated. CTC counts, however, were similar to that observed for metastatic PDAC disease. Upon the initiation of surgery and laparoscopic inspection of the pancreas and abdomen area of patients the diagnosis was changed to metastatic PDAC.

The methods described herein may also be used to compare the number of seprase+ cells to EpCAM+ CTCs derived from a tumor. The ratio of seprase expressing CTCs to EpCAM expressing CTCs may be used to determine metastatic potential of the tumor. Analysis of CTCs enumerated at both affinity beds for individual patients presented with different diseases showed varying dominating sub-population of cells. The data are summarized in Table 3. A higher number of Fap+ CTCs were observed in localized PDAC and metastatic colorectal cancer, while EpCAM+ cells were observed to be dominant in metastatic melanoma and metastatic PDAC. Median number for the FAPα/EpCAM ratio was 1.21, 1.16, 0.87, 0.69 for local PDAC, metastatic colorectal cancer, metastatic PDAC, and metastatic melanoma, respectively. Enumeration of these two sub-populations and their ratios may serve as a marker indicating stage of the disease.

TABLE 3

Ratio of seprase to EpCAM expression in CTCs from various cancers

| Ratio of Fapα to EpCAM cells | Localized PDAC (n = 28) | Metastatic PDAC (n = 16) | Metastatic CRC (n = 6) | Metastatic Melanoma (n = 11) |
|---|---|---|---|---|
| Fapα ≥ EpCAM | 70% | 44% | 83% | 36% |
| EpCAM > Fapα | 30% | 56% | 17% | 64% |

Example 3

Expression Analysis of CTCs Captured with Seprase-Targeting Affinity Reagent

Using the methods described herein, CTCs were captured, released, enumerated via impedance detection (no staining performed), and collected in a microtube. The collected CTCs were spun spin down and lysed using ~20 µL of lysing solution from a commercially available Cell-to-CT™ kit (Life Technologies, Grand Island, N.Y.). Cells-to-CT™ technology enables reverse transcription of lysates from $10$-$10^5$ cells without isolating or purifying RNA. Eliminating the RNA isolation step substantially expedites and simplifies gene expression analysis of cells. As an alternative, CTCs lysis and isolation of RNA was performed directly using the CTC capture bed. This can be performed when another set of serially connected chips, modified with FAPα and EpCAM, is used to enumerate cells and characterize their phenotype via immunostaining.

Samples after lysis were treated with DNase to remove residual gDNA from the total RNA (TRNA) sample. Both positive and negative (no RT enzyme) reverse transcription reactions were performed with 10 µL of TRNA from CTCs in a total volume of 50 µL. RT reaction were performed with M-MulV at 37° C. for 60 minutes. Quantitative real time PCR was performed to evaluate 15 gene expression levels using a SYBR green assay on a 7900HT Applied Biosystems instrument equipped with a 384 well plate. Both captured seprase+ and EpCAM+ CTC gene expression profiles were collected. The following genes (i.e., epithelial, mesenchymal, EMT, and CSC (Cancer Stem Cells) markers) were evaluated: EpCAM, KRAS, CD133, CD146, KRT19, CD34, GAPDH, CD24, FAP, ACT2, VIM, NANOG, CD44, CXCR4 and TWIST1 (Table 4).

TABLE 4

Gene expression markers evaluated in isolated CTCs

| Gene | Function/Implicaiton |
|---|---|
| EpCAM | Epithelial marker |
| KRAS | Oncogene, potentially contains mutation |
| CD133 | CD133+ shows properties of CSC |
| CD146 | Activator of EMT |
| KRT19 | Epithelial marker |
| CD34 | Normal hematopoietic marker |
| GADPH | Housekeeping gene |
| CD24 | Oncogene overexpressed in many human malignancies. CD24+ CD44+ EpCAM+ cells have 100 fold increased tumorigenic potential |
| Fap | Fibroblast (CAF) marker |
| Act2 | EMT marker, activation associated with poor prognosis |
| VIM | Upregulated during EMT |
| NANOG | Marker of CSC |
| CD44 | Involved in cell proliferation, differentiation, migration, signaling for cell survival and in angiogenesis. Associated with pathological activities of cancer cells. |
| CXCR4 | Overexpressed in solid epithelial cancers, has been observed to lead to metastasis |
| TWIST1 | Upregulated during EMT |

All genes expression values were normalized to the expression level of GAPDH, a housekeeping gene. The efficiencies of amplifications with each primer couple at different annealing temperatures were evaluated first, upon which, the optimal thermal cycling conditions were determined for qPCR of cDNA synthesized from CTCs' mRNA. Ten µL PCR volume contained 1-2 µL of synthesized cDNA.

Expression level of EpCAM mRNA in EpCAM+ CTCs was compared among different diseases. The highest expression was observed in metastatic melanoma and metastatic colorectal cancer. For both localized and metastatic PDAC, EpCAM mRNA expression levels were low, with the lowest for metastatic PDAC. Quantified EpCAM mRNA showed wide range of expression levels (4 orders of magnitude) in isolated CTCs. Assuming correlation of mRNA and protein expression, the aforementioned observation would indicate that the CTC capture device is able to isolate CTCs even with low expression of antigens on the cell surface.

While the invention has been described in detail with reference to specific examples, it will be apparent to one skilled in the art that various modifications can be made within the scope of this invention. Thus, the scope of the invention should not be limited by the examples described herein, but by the claims presented below.

We claim:

1. A method of capturing circulating tumor cells from a sample comprising:
   i) contacting the sample with a mammalian seprase-targeting affinity reagent;
   ii) contacting the sample with a mammalian EpCAM-targeting affinity reagent; and
   iii) capturing the cells retained in steps (i) and (ii), thereby capturing circulating tumor cells from the sample.

2. The method of claim 1, wherein the seprase-targeting affinity reagent and EpCAM-targeting affinity reagent are each immobilized on a surface of a solid support.

3. The method of claim 1, wherein the seprase-targeting affinity reagent is a competitive or a non-competitive inhibitor of seprase.

4. The method of claim 1, wherein the seprase-targeting affinity reagent is an antibody.

5. The method of claim 1, wherein the seprase-targeting affinity reagent is a nucleic acid aptamer or a peptide aptamer.

6. The method of claim 1, wherein the seprase-targeting affinity reagent is a peptide ligand of seprase.

7. The method of claim 6, wherein the peptide is selected from Ac-Gly-prolineboronic acid (Ac-Gly-BoroPro) and proline diphenyl phosphonate (Gly-ProP(OPh)$_2$).

8. The method of claim 1, wherein the EpCAM-targeting affinity reagent is an antibody.

9. The method of claim 1, wherein the seprase-targeting and EpCAM-targeting affinity reagents are contacted consecutively.

10. The method of claim 1, wherein the seprase-targeting and EpCAM-targeting affinity reagents are contacted simultaneously.

11. The method of claim 2, wherein the solid support is a part of a microfluidic device.

12. The method of claim 1 further comprising a step of releasing the captured circulating tumor cells.

13. The method of claim 12 where releasing is accomplished by addition of excess of soluble seprase-binding agent.

14. The method of claim 12 where releasing is accomplished by addition of an avidin compound.

15. The method of claim 12 where releasing is accomplished by photocleavage of a bifunctional linker.

16. The method of claim 15 where the bifunctional linker carriers a site that can be enzymatically cleaved.

17. The method of claim 15 where the bifunctional linker carriers a site that can be chemically cleaved.

18. The method of claim 1, wherein the sample is a blood sample from a patient carrying a tumor.

19. The method of claim 18, wherein the tumor is selected from melanoma, colorectal cancer, pancreatic ductal adenocarcinoma and prostate cancer.

20. The method of claim 1 further comprising a step of detecting one or more of the following biomarkers: EpCAM, CD146, CK5, CK7, CK18, CK19, CD44, Cd44v6, EphB4, IGF-1R, BCL2, HER2, HER3, CA19-9, CEA, CD133, MUC1, N-cadherin, Survivin, EGFR, KRAS, BRAF, p53, Pi3KCA, PTEN, KRT19, CD34, CD24, ACT2, VIM, NANOG, CXCR4 and TWIST1 in the captured cells.

21. The method of claim 1, wherein the sample comprises whole blood, body fluid, any cell-containing blood fraction, or a cell culture established from a patient's sample.

22. The method of claim 1, further comprising detecting seprase and EpCAM on the captured cells.

23. The method of claim 22, further comprising determining the ratio of seprase expressing cells to EpCAM expressing cells.

* * * * *